United States Patent [19]

Grollier et al.

[11] Patent Number: 4,604,282

[45] Date of Patent: Aug. 5, 1986

[54] CAPILLARY COSMETIC COMPOSITION CONTAINING A SARSAPARILLA EXTRACT

[75] Inventors: Jean-François Grollier, Paris; Josiane Allec, Pierrefitte, both of France

[73] Assignee: L'Oreal, Paris, France

[21] Appl. No.: 412,270

[22] Filed: Aug. 27, 1982

Related U.S. Application Data

[63] Continuation of Ser. No. 146,371, May 2, 1980, abandoned.

[30] Foreign Application Priority Data

May 15, 1979 [LU] Luxembourg ............................ 81257

[51] Int. Cl.$^4$ .......................... A61K 7/06; C11D 9/22; C11D 15/04
[52] U.S. Cl. ...................................... 424/74; 252/132; 252/DIG. 13; 424/DIG. 4
[58] Field of Search ........................... 424/74, DIG. 4; 252/132, DIG. 13

[56] References Cited

U.S. PATENT DOCUMENTS

| | | | |
|---|---|---|---|
| 3,904,748 | 9/1975 | Eckert et al. | 424/71 |
| 3,980,769 | 9/1976 | Ghilardi | 424/71 |
| 4,349,532 | 9/1982 | Vanlerberghe et al. | 424/70 |

OTHER PUBLICATIONS

De Navarre, *The Chem. and Manufacture of Cosmetics*, 2nd ed. pp. 42–45; 290–292 (1962).
Harry, *Principles & Practice of Modern Cosmetics*, vol. 2, pp. 403–404 (1963).
Bergwein, *Amer. Perfumes & Cosmetics*, vol. 83, pp. 41–43 (May 1968).
Sagarin, *Cosmetics, Science & Technology*, 1957, p. 385.

*Primary Examiner*—Albert T. Meyers
*Assistant Examiner*—Freda Abramson
*Attorney, Agent, or Firm*—Cushman, Darby & Cushman

[57] ABSTRACT

A capillary cosmetic composition for the washing and care of the hair comprises in an appropriate cosmetic vehicle an effective amount of at least one extract of sarsaparilla.

3 Claims, No Drawings

CAPILLARY COSMETIC COMPOSITION CONTAINING A SARSAPARILLA EXTRACT

This is a continuation of application Ser. No. 146,371 filed May 2, 1980, now abandoned.

The present invention relates to a capillary composition, principally for the washing and care of the hair, this composition containing as an active component an extract of sarsaparilla (Smilax species), a plant belonging to the liliaceous family.

Certain plant extracts have been and are now currently being used for washing hair. In particular, a decoction of Panama bark, of Saponaria and of ivy are being employed for this purpose.

The characteristics of these extracts are due principally to the presence of a complex mixture, and principally, of saponins which have been shown to impart to the compositions containing them a certain detergent activity.

However, it has been established that all plants containing saponins cannot be used effectively in compositions in the form of shampoos. Certain ones of these extracts are toxic or possess detergent properties insufficient to be effectively employed in cosmetic formulations.

Moreover, some plant extracts currently being used, such as those of Panama bark, exhibit certain disadvantages which make them difficult to use in certain types of compositions such as, for example, in shampoos for children since these extracts cause some irritation, principally of the ocular mucous.

The present invention resides in the surprising discovery that an extract of sarsaparilla (Smilax species) has the advantage of exhibiting good cosmetic and detergent characteristics, while at the same time, not only being practically devoid of toxicity, but also not causing any irritation or stinging sensations when inadvertently the composition comes into contact with the ocular mucous.

Besides, it has been observed, as opposed to certain other plant extracts, that the sarsaparilla extract can effectively retard a re-oiliness of hair.

The sarsaparilla extracts have previously been proposed for use as a medicinal substance which can be administered orally, principally for use as a depurative and in the treatment of nutritional disorders and syphilis. Such extracts, to the applicants' knowledge, have never been contemplated for use as the active principle in a cosmetic composition for the washing and care of the hair.

The present invention thus relates to a new industrial product comprising a capillary composition for the washing and care of the hair, the said composition comprising, in suitable cosmetic vehicle, at least one extract of sarsaparilla (Smilax species).

Sarsaparilla is a plant of the liliaceous family which includes many varieties, depending on their origin. Representative varieties or species of which the extract can be used in the composition of the present invention include:

*Smilax aspera, Smilax officinalis, Smilax regilii, Smilax glaberrina, Smilax medica, Smilax aristolochiaefolia, Smilax papyraceae, Smilax febrifuga, Smilax ornata, Smilax saluberina* and *Smilax china.*

These different varieties are found in various geographical areas such as southern Europe, Central America, Brazil, the Equator, Mexico and the like.

The sarsaparilla extract used in the composition of the present invention can be obtained essentially from the roots of the plant. These extracts are characterized by the presence of saponins, the sapogenins of which have a steroidic structure.

The sarsaparilla extract can be obtained in accordance with various processes and, principally, by maceration, digestion, decoction, infusion or lixiviation.

All these extraction methods are well known and are described in detail in the book: "L'Officine", by Dorvault, Edition Vigot, 1978, pp. 569-573.

The extracts of sarsaparilla obtained by these extraction processes can be provided in the form of a liquid extract, a dry extract or an extract of soft consistency. Preferably, according to the invention, a dry extract provided in the form of a powder with a characteristic odor is employed.

Of the various extraction processes, the preferred process, in accordance with the present invention is either an aqueous extraction at the boiling point of the solvent (preferably water), or lixiviation, using (1) at least one lower aliphatic alcohol having 1-3 carbon atoms such as methyl alcohol, ethyl alcohol or isopropyl alcohol of which the alcohol concentration is between 20° and 100°, and preferably between 65° and 75°, or (2) a mixture of water and ethyl acetate or acetone. This lixiviation type extraction can be carried out preferably at ambient temperature.

Particularly, there can be used the process described in French Pat. No. 1,520,375. This process comprises treating the roots of sarsaparilla ground in the presence of methyl, ethyl or isopropyl alcohol, at about 70°, and concentrating the resulting product under a vacuum until it has a pasty consistency. The extract obtained is then taken up in boiling water, which is then cooled and the insoluble portion filtered off. The fraction soluble in water can then be concentrated so as to provide liquid or dry extracts or it can optionally be treated again so as to yield extracts which are more pure or which are more enriched in active substances.

The soluble fraction can, in effect, be treated with ammonium sulfate and the resulting precipitate can be extracted with methanol or ethanol. After evaporation, a dry extract in the form of a powder is obtained which represents about, on a weight basis, from 8 to 10% of the total weight of the initially treated roots.

A decoction process can also be employed. This process involves boiling the ground roots of sarsaparilla in water for about 15-30 minutes. Thereafter, the insolubles are filtered off.

The sarsaparilla extract, expressed on a dry basis, is present in the cosmetic composition of the present invention in an amount of 0.1 to 20 percent by weight and preferably between 0.5 and 10 percent by weight relative to the total weight of the composition.

The pH of the composition is generally between 3 and 8.5 and preferably between 4 and 8.

The composition according to the present invention can optionally contain other plant extracts such as, for example, the extracts of Saponaria, of ivy, of Equisetum, and the like.

The cosmetic composition according to the present invention is provided, preferably, in the form of a shampoo.

These shampoos can be provided under various forms: either in the form of a dilute solution of the sarsaparilla extract obtained by decoction, in which case a significant amount of liquid in the order of 1-2 liters is necessary to wash the hair; or in the form of a concentrated solution of the sarsaparilla extract containing other surfactants, in which case an amount in the order of only 20 to 80 grams is necessary to wash the hair.

All the shampoos have a clear, opaque or pearly liquid appearance.

The shampoos, in accordance with the invention, can also contain various conventionally employed components such as perfumes, dyes, thickening agents such as fatty acid alkanolamides, preservatives, antioxidants and the like.

These compositions in the form of shampoos can also contain an anionic, nonionic, cationic or amphoteric surfactant, or a mixture thereof.

Representative anionic surfactants include, for instance, the following compounds as well as mixtures thereof: the alkaline salts, the ammonium salts, the amine salts or the amino alcohol salts of the following compounds:

(1) alkylsulfates, alkylether sulfates, alkylamide sulfates and ether sulfates, alkylarylpolyether sulfates and monoglyceride sulfates,
(2) alkyl sulfonates, alkylamide sulfonates, alkylaryl sulfonates and olein sulfonates,
(3) alkylsulfosuccinates, alkylethersulfosuccinates and alkylamide sulfosuccinates,
(4) alkylsulfosuccinamates,
(5) alkylsulfoacetates and alkylpolyglycerol carboxylates,
(6) alkyl phosphates and alkylether phosphates,
(7) alkylsarcosinates, alkylpolypeptidates and alkylaminodopolypeptides, wherein the alkyl radical in all these compounds listed in (1)–(7) above is a linear chain having 12–18 carbon atoms; and (8) fatty acids such as oleic acid, ricinoleic acid, palmitic acid, stearic acid, copra oil acids or hydrogenated copra oil acids, carboxylic acids of polyglycol ethers having the formula, $Alk-(OCH_2-CH_2)_n-OCH_2-CO_2H$, where Alk is a linear chain having 12 to 18 carbon atoms and where n is a whole number between 5 and 15.

Representative nonionic surfactants which can be used include the condensation products of a monoalcohol, an $\alpha$-diol, an alkylphenol, an amide or a diglycolamide with glycidol, such as, for example, compounds having the formula, $R_4-CHOH-CH_2-O-(CH_2-CHOH-CH_2-O)_p H$, wherein R represents an aliphatic, cycloaliphatic or arylaliphatic radical having, preferably, between 7 and 21 carbon atoms and mixtures thereof, the aliphatic chains being able to have ether, thioether or hydroxymethylene groups, and where p is between 1 and 10, inclusive, such as described in French Pat. No. 2.091.516; compounds having the formula, $R_5O-(C_2H_3O-(CH_2OH))_q H$, wherein $R_5$ represents alkyl, alkenyl or alkylaryl and q is a statistical value between 1 and 10, inclusive, such as described in French Pat. No. 1.477.048; compounds having the formula:

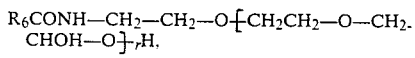

wherein $R_6$ represents an aliphatic radical or mixture of aliphatic radicals, linear or branched, saturated or unsaturated having, optionally, one or more hydroxyl groups and having from 8 to 30 carbon atoms and being of natural or synthetic origin, r representing a whole or decimal number from 1 to 5, designates the average degree of condensation, these compounds being described in French Pat. No. 2.328.763.

Other compounds included in this class are alcohols, alkylphenols, polyethoxylated or polyglycerolated fatty acids with a linear fatty chain having 8 to 18 carbon atoms and containing most often from 2 to 30 moles of ethylene oxide. Also usefully employed are copolymers of ethylene and propylene oxides, condensates of ethylene and propylene oxides on fatty alcohols, polyethoxylated fatty amides, polyethoxylated fatty amines, ethanolamides, fatty acid esters of glycol, fatty acid esters of sorbital and fatty acid esters of sucrose.

Representative cationic surfactants which can be used, alone or in admixture, include, particularly, salts of fatty amines such as alkylamine acetates, quaternary ammonium salts such as alkyldimethylbenzylammonium chloride or bromide, alkyltrimethylammonium chloride or bromide, alkyldimethylhydroxyethylammonium chloride or bromide, dimethyldistearylammonium chloride or bromide, alkylamido ethyltrimethylammonium methosulfates, alkylpyridinium salts and imidazoline derivatives. The alkyl radicals in these compounds have, preferably, between 1 and 22 carbon atoms. Also usefully employed are compounds having a cationic character, such as amine oxides, for instance, alkyldimethylamine oxides or alkylaminoethyl dimethylamine oxides.

Representative amphoteric surfactants that can be used include, more particularly, alkylamino mono- and dipropionates, betaines such as N-alkylsulfobetaines and N-alkylamidobetaines, cycloimidiniums such as alkylimidazolines, and asparagine derivatives. The alkyl group in these surfactants represents, preferably, one having between 1 and 22 carbon atoms.

The preferred surfactants are those exhibiting weak toxicity, such as, for example: polyoxyethylenated sorbitan monooleate or polyoxyethylenated sorbitan monolaurate, sold under the commercial names of "Tween 80" and "Tween 20" by Atlas; the condensation products of copra acids and animal protein hydrolyzates such as the potassium salt of the condensate of coconut oil and collagen polypeptides sold by Grunau; products of the formula, $R-(OCH_2-CH_2)_x-OCH_2-COOH$ wherein R is generally a $C_{12}$ to $C_{14}$ alkyl radical and x ranges from 6 to 10, such as "Sandopan DCT AC" sold by Sandoz and "Akypo RLM 100" sold by Chem Y; alkyl glucoside sold under the trade name "Triton CG 110" by Rohm & Haas; alkylimidazoline sold under the trade name "MIRANOL C2M" by Miranol; nonionic surfactants having the formula, $R_4-CHOH-CH_2-O-(CH_2-CHOH-CH_2-O)_p H$ where $R_4$ represents a mixture of alkyl radicals having between 9 and 12 carbon atoms and p has a statistical value of 3.5; a compound of the formula $R_5-O-(C_2H_3O(CH_2OH))_q H$ wherein $R_5$ represents $C_{12}H_{25}$ and q has a statistical value of 4 to 5; and a compound of the formula $R_6-(CONH-CH_2-CH_2-O-CH_2-CH_2-O-CH_2-CHOH-CH_2O)_r H$ wherein $R_6$ represents a mixture of radicals derived from lauric acid, myristic acid, oleic acid and copra acids and wherein r has a statistical value of 3 to 4.

The compositions according to the present invention can also be provided in the form of lotions called "rinse" lotions, these compositions being applied to the hair before or after a shampoo.

The lotions can be an aqueous or hydroalcoholic solution, an emulsion, a thickened lotion or a gel.

They can contain insoluble compounds such as pulverized vegetables, talc or clay so as to obtain a product having the appearance of cataplasm.

The compositions according to the present invention can also be provided in the form of hair styling lotions or a forming lotion, also called a brushing lotion, and a non-rinse hair lotion for reinforcing a hair set.

In order to better understand the invention, the following non-limiting examples of cosmetic compositions for the hair containing a sarsaparilla extract are given.

EXAMPLES OF COMPOSITIONS

Example A—Shampoo

Dry extract of sarsaparilla: 5 g
Natural extract of carrageen, sold under the trade name "Satiagum Standard" by Pierrefitte Auby: 0.2 g
5-bromo-5-nitro-1,3-dioxane: 0.03 g
Citric acid, sufficient amount for pH 4
Water, sufficient amount for: 100 g Example B—Shampoo Dry extract of sarsaparilla: 3 g
Dry extract of Saponaria: 2 g
5-bromo-5-nitro-1,3-dioxane: 0.03 g
Citric acid, sufficient amount for pH 4
Water, sufficient amount for: 100 g The shampoos according to Examples A and B provide a good washing of the hair and principally children's hair, without causing an irritation or stinging of the eyes.

The hair thus treated is flexible, shiny and pleasant to the touch.

Example C—After shampoo "rinse" composition

Dry extract of sarsaparilla: 2 g
Guar gum sold under the commercial name of "Vidogum GH 175" by Unipectine: 1.75 g
Avocado oil: 3 g
5-bromo-5-nitro-1,3-dioxane: 0.05 g
Water, sufficient amount for 100 g
This composition has a pH of 4.6.

After washing the hair and rinsing it with water, a sufficient and effective amount of the immediately proceding composition is applied to the hair so as to completely impregnate the hair. The composition is permitted to remain in contact with the hair for a few minutes, after which the hair is thoroughly rinsed with water.

The hair thus treated is flexible; it untangles easily and it is pleasant to the touch.

Example D—Shampoo

Dry extract of sarsaparilla: 2 g
Dry extract of Saponaria: 2 g
"Lamepon S" (potassium salt of the condensate of coconut oil and collagen polypetides having an average molecular weight of 700 to 800, a density at 20° C. of 1.05 to 1.07, a pH in a 10% solution of 6.0 to 6.5 and a viscosity at 20° C. of 1500 to 5000 centipoises): 6 g
Carob bean gum, sold under the trade name "Lyogomme 6" by Pierrefitte Auby: 0.5 g
5-bromo-5-nitro-1,3-dioxane: 0.03 g
Citric acid, sufficient amount for pH 5.5
Water, sufficient amount for: 100 g Example E—Shampoo Dry extract of sarsaparilla: 5 g
"Tween 20", polyoxyethylenated sorbitan monolaurate: 2 g (M.A.)
Carob bean gum, sold under the trade name "Lygomme 6": 0.5 g
5-bromo-5-nitro-1,3-dioxane: 0.03 g
Water, sufficient amount for: 100 g
The pH of this composition is 4.5.

After washing the hair using a sufficient amount of the shampoos of Examples D and E followed by rinsing the hair with water, it is observed that the hair is flexible and untangles easily. The use of these shampoos also avoids rapid re-oiling of the hair.

Example F—Non-rinse lotion

Dry extract of sarsaparilla: 0.5 g
Polyvinyl pyrrolidone/vinyl acetate copolymer, (60/40): 0.2 g
Ethyl alcohol sufficient amount for 10°
Water, sufficient amount for: 100 g
The pH of this composition is 7.

Example G—Before shampoo rinse compoition

Dry extract of sarsaparilla: 2.5 g
5-bromo-5-nitro-1,3-dioxane: 0.03 g
Citric acid, sufficient amount for pH 4
Water, sufficient amount for: 100 g Example H—Shampoo Dry extract of sarsaparilla: 7 g
$C_{12}$–$C_{18}$ alkyl dimethylcarboxymethyl ammonium hydroxide, sold under the commercial name, "Dehyton AB 30" by Henkel: 3 g (M.A.)
Sodium orthophenylphenate: 0.3 g
Citric acid, sufficient amount for pH 4
Water, sufficient amount for: 100 g Example I—Shampoo Dry extract of sarsaparilla: 4 g
Alkyl glucoside of the formula:

$$\left[ \begin{array}{c} CH_2OH \\ OH \\ OH \end{array} \begin{array}{c} O \\ \end{array} OR \right]_x$$

wherein $X = 1$ to 5 and $R = C_8$ to $C_{20}$ alkyl, sold under the trade name of
"Triton CG 110" by Rohm & Haas: 3 g (M.A.)
5-bromo-5-nitro-1,3-dioxane: 0.03 g
Triethanolamine, sufficient amount for pH 4.5
Water, sufficient amount for: 100 g Example J—Shampoo Dry extract of sarsaparilla: 0.1 g
Nonionic surfactant of the formula:

$$R\text{—}CHOH\text{—}CH_2O\text{—}[CH_2\text{—}CHOH\text{—}CH_2O]_n\text{—}H$$

wherein $R = C_9$–$C_{12}$ alkyl and n has a statistical value of 3.5: 15 g
5-bromo-5-nitro-1,3-dioxane: 0.03 g
Water, sufficient amount for: 100 g
The pH of this composition is 5.

Example K—Shampoo

Dry extract of sarsaparilla: 10 g
Nonionic surfactant of the formula:

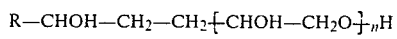

wherein R is $C_9$–$C_{12}$ alkyl and n has a statistical value of 3.5: 2 g
5-bromo-5-nitro-1,3-dioxane: 0.03 g
Water, sufficient amount for: 100 g
The pH of this composition is 5.

Example L—Before shampoo composition

Dry extract of sarsaparilla: 4 g
*Cassia Obovata* pulverized powder, sufficient amount for: 100 g This mixture is employed in making a paste with water. The resulting cataplasm is applied to soiled hair and is permitted to remain in contact therewith for 30 minutes. Thereafter, the hair is shampooed. After several weeks of this treatment, it is observed that the hair re-oils less rapidly.

Example M—After shampoo composition

Dry extract of sarsaparilla: 8 g
Kaolin, sufficient amount for: 100 g

This mixture is employed in making a paste with water. The resulting cataplasm is applied to clean hair and is permitted to remain in contact therewith for 15 minutes. Thereafter, the hair is rinsed. After a few weeks of this treatment, it is observed that the hair re-oils less rapidly.

Example N

A hair washing composition is prepared by boiling 200 g of ground sarsaparilla roots in two liters of water for 20 minutes. After cooling, the insolubles are filtered off, yielding about 1.5 liters of a 2% solution of dry extract that is effectively employed to wash the hair.

What is claimed is:

1. A method for washing the hair, comprising applying thereto an effective amount, so as to completely impregnate the hair, of a composition containing in an aqueous carrier from 0.1 to 20 weight percent of a sarsaparilla dry extract obtained from the ground roots of *Smilax medica*, said extract containing saponins, the sapogenin of said saponins having a steroidic structure, and said composition having a pH between 4 and 8.

2. The method of claim 1 wherein said composition also includes an effective amount of an anionic, nonionic, cationic or amphoteric surfactant, or a mixture thereof.

3. The method of claim 1 wherein said composition is an aqueous solution of said sarsaparilla extract present in an amount, expressed on a dry basis, ranging from 0.5 to 10 weight percent based on the total weight of said composition.

* * * * *